(12) United States Patent
Christ

(10) Patent No.: US 11,761,881 B2
(45) Date of Patent: Sep. 19, 2023

(54) SYSTEM FOR MICROSCOPIC EXAMINATION OF AN INCUBATED SAMPLE

(71) Applicant: Leica Microsystems CMS GmbH, Wetzlar (DE)

(72) Inventor: Stefan Christ, Schoeffengrund (DE)

(73) Assignee: LEICA MICROSYSTEMS CMS GMBH, Wetzlar (DE)

( * ) Notice: Subject to any disclaimer, the term of this patent is extended or adjusted under 35 U.S.C. 154(b) by 77 days.

(21) Appl. No.: 17/233,400

(22) Filed: Apr. 16, 2021

(65) Prior Publication Data
US 2021/0333197 A1    Oct. 28, 2021

(30) Foreign Application Priority Data
Apr. 28, 2020  (EP) .................................. 20171923

(51) Int. Cl.
*G01N 21/01* (2006.01)
*G02B 21/06* (2006.01)

(52) U.S. Cl.
CPC ............. *G01N 21/01* (2013.01); *G02B 21/06* (2013.01)

(58) Field of Classification Search
CPC ........ G01N 21/01; G02B 21/06; G02B 21/28; G02B 21/30; G02B 21/24; C12M 41/14; C12M 41/36; C12M 41/48; C12M 23/04; C12M 23/38; C12M 29/00; C12M 29/26; C12M 41/00; C12M 41/12; C12M 41/20; C12M 41/34; C12M 41/46
USPC .......................................................... 359/385
See application file for complete search history.

(56) References Cited

U.S. PATENT DOCUMENTS

| | | | |
|---|---|---|---|
| 2006/0023299 A1* | 2/2006 | Muraki ................. | C12M 41/14 359/368 |
| 2008/0247038 A1* | 10/2008 | Sasaki ............... | G02B 21/0088 359/395 |
| 2009/0086316 A1* | 4/2009 | Kawahito ............. | G02B 21/30 359/395 |

FOREIGN PATENT DOCUMENTS

WO       WO-9605285 A1 *  2/1996    ............ C12M 27/12

OTHER PUBLICATIONS

Microscopy from Carl Zeiss, Cells Need the Perfect Climate, System Solutions for Live Cell Imaging under Physiological Conditions, Feb. 2008.

* cited by examiner

*Primary Examiner* — Balram T Parbadia
*Assistant Examiner* — Rahman Abdur
(74) *Attorney, Agent, or Firm* — Patentbar International (57) ABSTRACT

A system for microscopic examination of a sample has a microscope and an incubation environment conditioning unit connected to the microscope. The microscope has a microscope housing enclosing an illumination optics, a microscope stage and an imaging optics, an integrated sample chamber located within the microscope housing and formed by a separated housing section within the microscope housing. The housing section has a microscope interface for connecting the incubation environment conditioning unit to the sample chamber and/or to a stage top chamber for placing within the sample chamber and for receiving the sample. The system provides a first and a second incubation modes. In the first incubation mode the sample chamber is incubated by supply of a first incubation atmosphere by the incubation environment conditioning unit. In the second incubation mode the stage top chamber is incubated by (Continued)

supply of a second incubation atmosphere by the incubation environment conditioning unit.

17 Claims, 6 Drawing Sheets

SYSTEM FOR MICROSCOPIC EXAMINATION OF AN INCUBATED SAMPLE

RELATED APPLICATIONS

This application claims priority to European Patent Application EP 20171923.4, filed Apr. 28, 2020, which is incorporated herein by reference in its entirety.

FIELD OF THE INVENTION

The present inventive concept is directed to a system for microscopic examination of a sample comprising a microscope and an incubation environment conditioning unit connected to said microscope, particularly for examination of a sample incubated in an incubation atmosphere adapted to the sample.

BACKGROUND OF THE INVENTION

Especially in the field of microscopic examination of living samples like cells, it is of great interest to keep the sample as long as possible under favourable and stress-free environmental conditions. To this end, incubators are used for generating a microclimate adapted to the sample to be examined. Existing incubators can be distinguished in stage top incubators, on the one hand, and cage incubators, on the other hand.

Cage incubators are mounted to a standard microscope, preferably an upright microscope, and comprise a large climatic chamber covering the main parts of the microscope, such as the objective revolver, the microscope stage including the sample carrier and a condenser, such that a large volume needs to be incubated. Access to the working area for placing or manipulating the sample is provided inside the cage incubator and can be reached through dedicated openings in the cage incubator walls. Especially due to these handling openings, the dimensions of the cage incubator are so large that it protrudes significantly beyond the microscope stand. Therefore, it is not possible to equip a microscope with a cage incubator in a space-saving manner. On the other hand, a stage top incubator provides a small volume to be incubated as the stage top incubator only encloses the sample itself and is placed onto the microscope stage. Even if a stage top incubator has minimum space requirements, access to the sample is minimal since the sample is surrounded by a sealed box which has to be opened, thus, destroying the incubation atmosphere within the box. Access to the sample to introduce additional equipment for manipulation of the sample is difficult if not impossible due to the tight space restrictions of a stage top incubator module. While a cage incubator has a high energy and gas consumption, a stage top incubator provides a small closed incubated room including connected supply conduits for supplying the desired incubation atmosphere. On the other hand, the stage top incubator module is able to quickly equilibrate any disturbance of the incubation atmosphere (e.g. after opening the module) or reach the desired setup as the exchanged air volume per time of a cage incubator usually exceeds that of a stage top incubator.

A stage top incubator allows close control of the direct incubation environment surrounding the sample, the regulated volume being reduced to a minimum, which allows quick changes to the incubation environment. However, access to the sample itself is very limited and, hitherto, the stage top solution adds significant complexity and a high price to the customer system. On the other hand, the cage incubator allows easier access to the sample, but it is slow when it comes to changing environmental conditions or reaching a set point of a predefined incubation atmosphere.

Up to now, customers need to install/purchase two discrete systems, namely a stage top incubator system and a cage incubator, in order to be able to flexibly examine various samples under different incubation environments and to use the benefits of either system. This, however, drives costs, complexity, and is not beneficial for usability of the overall system as each of the systems comes with its own control units and software.

SUMMARY OF THE INVENTION

In view of the drawbacks and problems described above, there is a need for an improved incubation solution in microscopy.

Embodiments of the present inventive concept provide a system for microscopic examination, also to be understood as imaging, of a sample comprising a microscope and an incubation environment conditioning unit connected to said microscope according to claim 1. The microscope of said system comprises a microscope housing enclosing an illumination optics, a microscope stage and an imaging optics, further an integrated sample chamber located within the microscope housing and formed by a separated housing section within said microscope housing, wherein said housing section comprises a microscope interface configured for connection of the incubation environment conditioning unit to the sample chamber and/or to a stage top chamber to be placed within said sample chamber and configured to receive the sample. The system provides a first incubation mode and a second incubation mode, wherein, in the first incubation mode, the sample chamber is incubated by supply of a first incubation atmosphere, and, in the second incubation mode, the stage top chamber is incubated by supply of a second incubation atmosphere by said incubation environment conditioning unit.

The present inventive concept can thus provide a microscope having a relatively large sample chamber formed by a separated housing section within the microscope housing, which sample chamber can be incubated by the connected incubation environment conditioning unit without having the large volumes involving high energy and gas consumption of a cage incubator. As a dedicated sample chamber is formed by a separated housing section, a larger incubation room can be designed compared to known stage top incubators, at the same time avoiding a bulky cage incubator arrangement. This incubation solution is thus also called "sample chamber incubator" in this application. At the same time, the system provides a stage top chamber to be placed within the sample chamber and configured to receive the sample. The wording "to be placed within the sample chamber" can also be used in the meaning of "to be formed/built within the sample chamber", as will be explained in more detail further below. The microscope interface of the system is also configured for connection of the incubation environment conditioning unit to the stage top chamber such that, in the second incubation mode, the stage top chamber is incubated by supply of a second incubation atmosphere by said conditioning unit.

The present inventive concept thus provides a customer with two incubation solutions realised in the same system. In the first incubation mode, the incubated volume is reduced to the volume of the separated housing section within the microscope housing, which is designed specifically to the needs of the respective microscope and intended applications so that the inside volume is already decreased to a minimum. The sample chamber allows for enough space to perform all necessary sample manipulations requested by the application and leaves enough space for additional necessary equipment. Still the system enables a user to make use of a stage top incubator without changing to another system. The present inventive concept combines a stage top and a sample chamber incubator in one single system and shares common components. In this system, it is preferred to have the sample chamber incubator as the default incubation solution. The incubation environment conditioning unit becomes the central, shared component for supplying a first and a second incubation atmosphere in the first and second incubation mode, respectively.

In an advantageous embodiment, the incubation environment conditioning unit comprises a pump control unit interface for connecting a first pump control unit and/or a second pump control unit, wherein the first pump control unit is configured to supply the first incubation atmosphere having a first group of parameters in the first incubation mode, and the second pump control unit is configured to supply the second incubation atmosphere having a second group of parameters in the second incubation mode. In this embodiment, the pump control units are configured to supply the corresponding incubation atmosphere in the respective incubation mode via the microscope interface to the sample chamber or to the stage top chamber. Each incubation atmosphere is defined by a group of parameters, particularly comprising at least one of a flow rate and a temperature and contents of $H_2O$ and/or $CO_2$ and/or $N_2$ and/or $O_2$. In microscopic live cell imaging, the incubation environment conditioning unit should typically be able to control temperature, humidity and $CO_2$ content of the incubation atmosphere. To this end, connections for supplying $H_2O$ and $CO_2$, remainder air, should be present. On the other hand, it may also be desirable to conduct hypoxia experiments where a reduced level of oxygen is present in the incubation atmosphere. This deprivation in oxygen is typically established by displacing oxygen with nitrogen ($N_2$) inside the incubation chamber. The desired incubation atmosphere having a corresponding group of parameters is supplied by one of the pump control units.

The pump control unit interface can either be configured for connecting both the first and the second pump control unit. In this case, depending on the selected incubation mode, one of the pump control units has to be addressed by the system. On the other hand, the pump control unit interface can be configured for connecting the first pump control unit, and for alternatively connecting the second pump control unit after removing the first pump control unit and vice versa. In this case it is preferred if the system is configured to automatically switch into the respective incubation mode depending on which pump control unit is connected to the pump control unit interface.

It is advantageous if the housing section of the microscope housing comprises a lid providing direct access to the microscope stage for accessing the sample in the sample chamber. In other words, the housing section comprises an opening or recess which is closable by a "lid" which term is meant to be understood also as a door or a hood or a window or other equivalent means for opening and closing. Particularly, the lid is a hinged lid. It is also advantageous if the housing section of the microscope housing is configured such that, when the lid is closed, the sample chamber is sealed. By sealing the sample chamber, any losses of incubation atmosphere due to leakage can be minimised. By opening the lid, a sample can be placed in the sample chamber, particularly on the microscope stage, a stage top chamber can be placed within the sample chamber and samples can be exchanged and/or manipulated. Instead of a lid providing direct access to the microscope stage, other solutions can be thought of like an automatic sample feed for transporting the sample onto the microscope stage.

In an advantageous embodiment, the microscope, in particular the housing section, comprises a common atmosphere regulation module for controlling the first group of parameters of the first incubation atmosphere in the first incubation mode, and the second group of parameters of the second incubation atmosphere in the second incubation mode. Such a common atmosphere regulation module, or, more generally, any atmosphere regulation module as further described below, can be used for further regulating or fine tuning of the incubation atmosphere. To this end, sensors may be provided in an atmosphere regulation module or at least sensor signals may be provided to an atmosphere regulation module, the sensors signals representing values of at least some of the parameters of the respective incubation atmosphere. If an actual value of such a parameter deviates from the setpoint of this parameter, the atmosphere regulation module can regulate/readjust the respective parameter. To this purpose, it is advantageous if the common atmosphere regulation module is in communication with the first pump control unit in the first incubation mode, and with the second pump control unit in the second incubation mode. As already pointed out, the same is true for other kinds of atmosphere regulation modules as described further below. In this embodiment, if the temperature or humidity of the incubation atmosphere deviates from the corresponding setpoints, the atmosphere regulation module can send a request to the corresponding pump control unit for regulating/readjusting the temperature or humidity to the correct setpoints. On the other hand, the atmosphere regulation module can be provided with corresponding means for such a regulation/readjustment. For example, the atmosphere regulation module may comprise a heater/cooler and/or a humidifier for regulating temperature and/or humidity of the incubation atmosphere on its own without communication with the corresponding pump control unit.

In another advantageous embodiment, the microscope, in particular the housing section, comprises an atmosphere regulation module interface for connecting a first atmosphere regulation module and/or a second atmosphere regulation module, wherein the first atmosphere regulation module is configured for controlling the first group of parameters of the first incubation atmosphere in the first incubation mode, and the second atmosphere regulation module is configured for controlling the second group of parameters of the second incubation atmosphere in the second incubation mode. In contrast to a common atmosphere regulation mode, this embodiment provides separate atmosphere regulation modules for regulating/readjusting the first or second incubation atmosphere in the first or second incubation mode. All other features described above in relation to the common atmosphere regulation module apply in the same way to the first and the second atmosphere regulation modules.

The atmosphere regulation module interface can be configured for connecting the first and the second atmosphere regulation modules at the same time. In this case, depending on the selected incubation mode, one of the first and second atmosphere regulation modules has to be addressed by the system. Alternatively, the atmosphere regulation module interface is configured for connecting the first atmosphere regulation module, and for alternatively connecting the second atmosphere regulation module after removing the first atmosphere regulation module and vice versa. In this case, it is preferred if the system is configured to automatically switch into the respective incubation mode depending on which atmosphere regulation module is connected to the interface. In an embodiment where first and second pump control units and first and second atmosphere regulation modules are present, two clear configurations exist to realise a first incubation mode ("sample chamber incubation") and a second incubation mode ("stage top incubation"). In the first incubation mode, the first pump control unit is connected to the pump control unit interface of the incubation environment conditioning unit and paired with the first atmosphere regulation module connected to the atmosphere regulation module interface in the microscope. For example, with such an arrangement, the temperature, the percent of $CO_2$-level and the relative humidity inside the sample chamber can be controlled. The overall set up allows free access to the sample and the use of additional modules, like a plate loader, a pipetting solution, etc.

On the other hand, in the second incubation mode, the first pump control module is swapped with the second pump control unit and the first atmosphere regulation module is swapped with the second atmosphere regulation module (either automatically or manually by the customer). Further, a stage top chamber is either placed or formed within the sample chamber, and, for examination, a sample is placed into the stage top chamber. With such an arrangement, for example, it is possible to control the temperature, the percent of $CO_2$, the percent of $O_2$ and the relative humidity inside the small volume of the stage top chamber. Oxygen depletion is achieved by displacement of oxygen with nitrogen ($N_2$) and humidity ($H_2O$).

Such a system providing the above two configurations for implementing a first and second incubation mode includes a number of advantages: the first and second pump control units connect to the same conditioning unit interface in both configurations. Same is true for the first and second atmosphere regulation modules which connect to the same atmosphere regulation module interface. The second incubation mode may also use the power supply, temperature control and means of heat distribution and machine interface as the first incubation mode. Further, both configurations are advantageously controlled by a mutual software interface as will be discussed further below.

Hitherto, oxygen depletion experiments in cage incubators are technically difficult to achieve as a huge volume of nitrogen is needed to flush oxygen out of the large incubation volume. This leads to a high complexity of the overall system to ensure air tightness and it requires additional safety measures at the customer site (e.g. gas alarm in laboratory, customer site inspection before installation, additional ventilation means in the laboratory). The inventive concept of a combination of a sample chamber incubator with a stage top incubator, particularly for oxygen depletion experiments, helps cap the costs of the overall system and operation, reduces complexity of the overall system and reduces the risks at the customer site.

In order to stay with the above examples, it is advantageous if the first atmosphere regulation module (or the common atmosphere regulation module) includes sensors for determining the temperature and/or the contents of $H_2O$ and/or $CO_2$ in the incubated sample chamber. Additionally or alternatively, corresponding sensors are arranged in the sample chamber and connected to the first atmosphere regulation module for delivering corresponding sensor signals to the first atmosphere regulation module. Similarly, it is advantageous if the second atmosphere regulation module includes sensors for determining the temperature and/or the contents of $O_2$ and/or $H_2O$ and/or $CO_2$ in the incubated stage top chamber. Additionally or alternatively, such sensors are arranged in the incubated stage top chamber and connected to the second atmosphere regulation module for providing corresponding sensor signals to the second atmosphere regulation module. These embodiments allow the first and second atmosphere regulation modules to better regulate/readjust the respective incubation atmosphere to the setpoint parameters.

As already mentioned above, it can be advantageous if an atmosphere regulation module, especially the second atmosphere regulation module, further includes a humidifier for humidifying the second incubation atmosphere independent from the incubation environment conditioning unit. By introducing $H_2O$ into the stage top chamber, relative humidity increases.

In general, it is advantageous if the system shares as many components as possible in the first and in the second incubation mode. Particularly, it is advantageous if the system comprises a common water pump configured to supply $H_2O$ to both the first and the second pump control units, unifying this user interface.

In another advantageous embodiment, in the second incubation mode, the system is configured to use the same temperature control and/or method for heat distribution as in the first incubation mode by controlling the temperature in the stage top chamber via the temperature in the sample chamber. As the temperature in the relatively small stage top chamber mainly depends on the temperature of the surrounding sample chamber, it is possible to control the temperature in the stage top chamber by controlling the temperature in the sample chamber. To this end, the incubation environment conditioning unit may e.g. provide a dedicated flow of air of the desired temperature into the sample chamber while at the same time the second pump control unit provides the second incubation atmosphere into the stage top chamber.

In a particularly advantageous embodiment, the system comprises a universal software interface for communication with a microscope controller, on the one hand, and for providing an incubation environment conditioning unit interface for communication with the incubation environment conditioning unit, on the other hand. The microscope controller is configured to control the functional components, like the imaging optics, the microscope stage and/or the illumination optics, of the microscope for controlling the microscopic examination/imaging of the sample and the workflow of the experiment. The universal software interface communicates with the microscope controller and with the incubation environment conditioning unit such that the microscope and the incubation environment conditioning unit can both be controlled/addressed by the universal software interface. In this connection, it is particularly advantageous if the universal software interface provides a corresponding graphical user interface (GUI) displayed on a display screen to the customer/user. The GUI is preferably adapted to the various possible kinds of experiments of the system according to the present inventive concept. In the above examples, the user can, for example, set the desired temperature, humidity and $CO_2$-content (and the desired $O_2$-content in case of hypoxia experiments) of the incubation atmosphere by selecting corresponding buttons in the GUI. Preferably, default values for the respective parameters are shown in the GUI, which can be changed by the user. Furthermore, parameters of functional components of the microscope can be set through the same GUI, e.g. illumination wavelength/intensity, camera parameters like sensitivity, gain, etc.

As already mentioned above, it is advantageous if the universal software interface is configured such that the system automatically switches into the first incubation mode if the first pump control unit is connected to the pump control unit interface, and into the second incubation mode if the second pump control unit is connected to the pump control unit interface. The universal software interface can be further configured such that it detects whether the right atmosphere regulation module is present in the microscope, for example, whether, in the first incubation mode, the first atmosphere regulation module is connected to the corresponding module interface or whether the common atmosphere regulation module is active.

Further, it is advantageous if the system comprises a sample holder for holding the sample in the first incubation mode, the sample holder being adapted for attachment of a cover for forming the stage top chamber to be used in the second incubation mode. Such an arrangement is particularly useful in order to avoid a cumbersome handling of the sample, e.g. out of the sample chamber and into a stage top chamber and back into the sample chamber or exchanging a sample by another sample in a stage top chamber. Rather, with this embodiment it is possible to examine/image a sample first in the first incubation mode, which sample is placed in a (universal) sample holder, and second in the second incubation mode after having attached a cover onto the sample holder for forming a stage top chamber enclosing the sample. In order to be able to introduce the second incubation atmosphere into the stage top chamber, it is advantageous if the sample holder includes a connection for introduction of gas/incubation atmosphere.

As used herein, the term "and/or" includes any and all combinations of one or more of the associated listed items and may be abbreviated as "/".

It should be noted that features of the above examples as well as of the examples explained below can—wholly or in part—be combined to other examples not explicitly mentioned herein, nevertheless being part of the present disclosure.

DETAILED DESCRIPTION OF THE PREFERRED EMBODIMENTS

Figure 1:
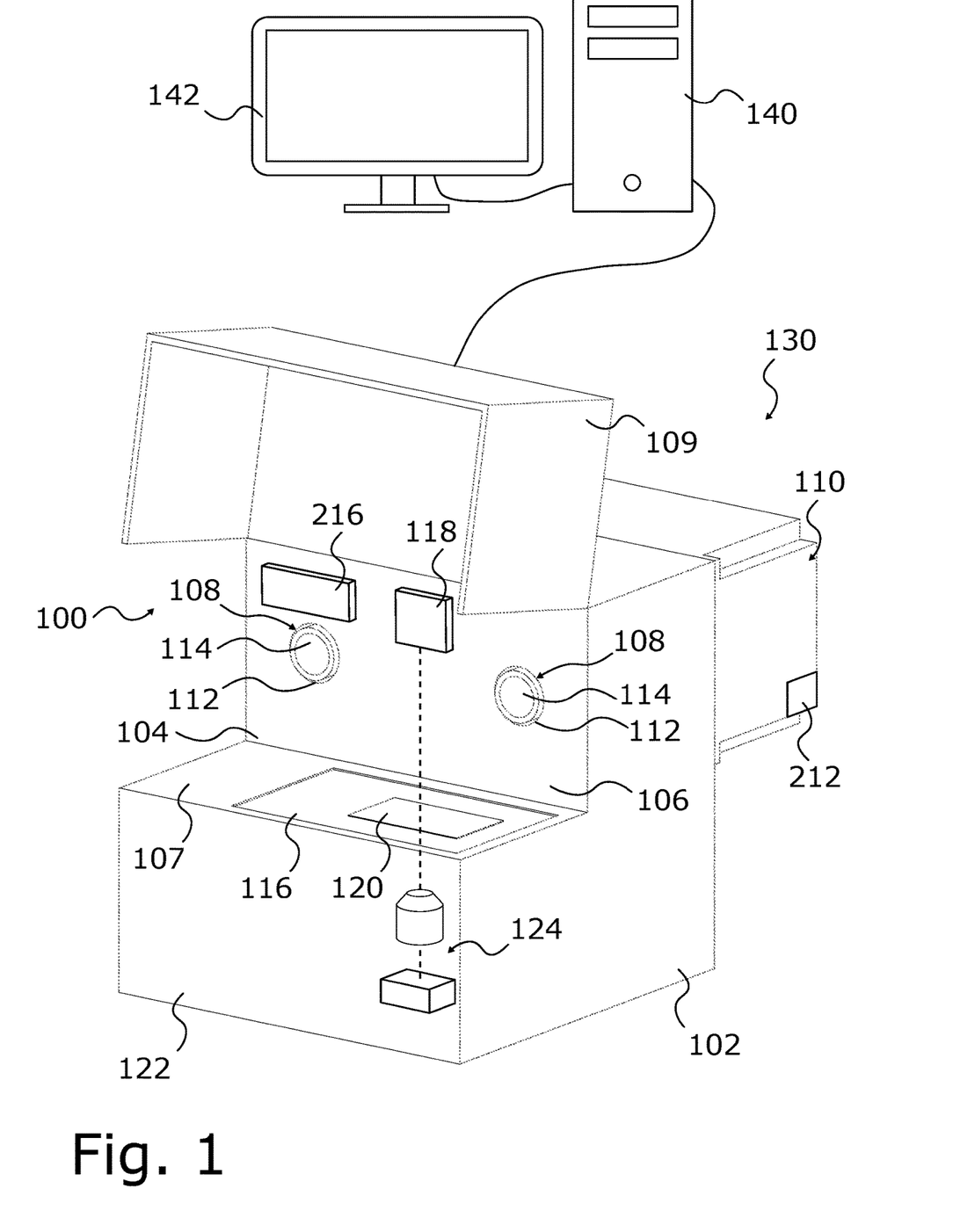
FIG. 1 schematically shows a perspective view of an embodiment of a system according to the inventive concept, FIGS. 2A, 2B, and 2C schematically show different configurations of embodiments of a system according to the inventive concept, and FIG. 3 schematically shows an embodiment of a system overview according to the inventive concept, and FIG. 4 schematically shows an embodiment of a stage top chamber used in a system according to the inventive concept.

FIG. 1 schematically shows in a perspective view an embodiment of a microscope 100 for microscopic examination of a sample 120 arranged on a microscope stage 116. A microscope housing 102 encloses an illumination optics 118, the microscope stage 116 and an imaging optics 124. An integrated sample chamber 106 is located within the microscope housing 102 and formed by a separated housing section 104 within said microscope housing 102. The housing section 104 comprises a hinged lid 109 which provides direct access to the microscope stage 116 for placing the sample 120 in the sample chamber 106 onto the microscope stage 116 and for exchanging samples 120 and/or manipulating samples 120 when the lid is opened. The embodiment shown in FIG. 1 is an inverse transmitted-light microscope 100 where the transmitted-light illumination optics 118 is arranged within the housing section 104, while the imaging optics is located below the microscope stage 116 in a second housing section 122. The imaging optics 124 typically includes a microscope objective and an image detector as the main components. The image detector usually comprises a camera which generates microscopic images which are typically displayed on a display screen 142 outside the microscope housing 102.

The construction of the microscope housing section 104 allows—after closing the lid 109—to form a dedicated sample chamber 106 which constitutes a preferably sealed space which can be incubated such that during microscopic examination/imaging of living samples 120 like cells, the sample can be kept under favorable and stress-free environmental conditions. To this end, the housing section 104 comprises an interface 108 for connection of an external incubation environment conditioning unit 110 to the sample chamber 106. The interface 108 is configured to provide a connection between the conditioning unit 110 and the sample chamber 106, such that environmental conditions in the sample chamber 106 can be controlled when the conditioning unit 110 is connected to the interface 108. This configuration implements the first incubation mode ("sample chamber incubation").

In the embodiment shown, the interface 108 as a part of the housing section 104 comprises two openings 112 in the backside of the housing section 104, each opening 112 being configured to receive a conduit 114. Incubation atmosphere can be introduced through at least one of the conduits 114 into the sample chamber 106. Depending on the leakage of the sample chamber 106, a part of the incubation atmosphere is allowed to escape the sample chamber 106. On the other hand, a part of the incubation atmosphere can be withdrawn from the sample chamber 106 via another one of the conduits 114.

Suitable incubation atmospheres comprise air with a predefined content of $H_2O$ (relative humidity) and a predefined content of $CO_2$ (carbon dioxide). It is also desirable to conduct hypoxia experiments with a deficiency of oxygen in the atmosphere. Typically, the temperature of the incubation atmosphere can be set in a range between ambient temperature of about 20° C. up to 50° C., especially between 25 and 37° C., the $CO_2$-range is set between 0.5 to 20%, and the $O_2$-range is set between 1 to 18%. The humidity must be balanced to ensure that potential condensation is avoided or at least does harm neither the microscope 100 nor the conditioning unit 110 nor the sample itself. It is preferred to control at least the temperature, the humidity and the $CO_2$-content on its own. In hypoxia experiments, the $O_2$-content is controlled by $N_2$-input. Such experiments are preferably conducted in the second incubation mode ("stage top chamber incubation") as will be explained further below.

In order to control the above parameters, it is preferred to arrange sensors in the conduits 114 and/or in the sample chamber 106 and/or at the microscope stage 116 close to the sample 120. In a preferred embodiment, at least some of the sensors are integrated into a conduit 114 for supplying incubation atmosphere to the sample chamber 106.

As shown in FIG. 1, the housing section 104 is bounded downward by a working surface 107 including an upper side of the microscope stage, in other words the microscope stage tabletop. This construction provides a user-friendly access to the working area for placing and manipulating the sample 120. To the other sides, the housing section is bounded by the inner sides of the lid 109 and the backside of the housing section 104 itself.

For increasing the live span of the imaging optics 124 and in case of using immersion objectives, it is preferred to air condition and/or temperature-control the second housing section 122. This can either be done by the same conditioning unit 110 and a correspondingly enlarged interface 108 or, more preferred, by a separate air conditioning unit.

In a preferred embodiment, the microscope 110 comprises a controlling unit 140 which can be or can include a microscope controller 350 (see FIG. 3) that controls functional components like the illumination optics 118, the microscope stage 116 and the imaging optics 124 of the microscope 100 for controlling the microscopic examination/imaging of the sample 120. Typically, a graphical user interface (GUI) is displayed on the display screen 142 for a user-friendly operation of the microscope 100. The controlling unit 140 is further configured to control the operation of the incubation environment conditioning unit 110 when the conditioning unit 110 is connected to the interface 108. Cables and lines for communication between the microscope controlling unit 140/microscope controller 350 and a conditioning unit controller (not shown) can be guided through one or more of the above openings/conduits of the interface 108. In this case, the same GUI may display corresponding buttons for setting desired values for the incubation atmosphere parameters as mentioned above. After confirmation that the lid 109 is closed and the sample to be examined is placed on the table of the microscope stage 116, generation of the user-defined incubation atmosphere automatically starts and, once the desired atmosphere is established and the sample 120 is in the right position, examination/imaging of the sample is carried out.

As shown in FIG. 1 the default configuration is the first incubation mode, namely, in this embodiment, the sample chamber incubation mode. As will be described in more detail in connection with the following figures, the incubation environment conditioning unit 110 comprises a pump control unit interface for connecting a first pump control unit 212 which is shown in FIG. 1. Within the housing section 104, at its backside, there is an atmosphere regulation module interface to which a first atmosphere regulation module 216 is connected to as shown in FIG. 1. The above mentioned sensors for detecting one or more of the incubation atmosphere parameters are preferably arranged in the sample chamber 106, particularly in or at the first atmosphere regulation module 216. The first atmosphere regulation module 216 is connected to the incubation environment conditioning unit 110 via a communication line. In that way, depending on the sensor signals which correspond to the parameter values, the first atmosphere regulation module 216 together with the first pump control unit 212 can provide a feedback control to set the first group of parameters of the first incubation atmosphere to a desired setpoint. This process will be further described in connection with the following figures.

Figure 2A:
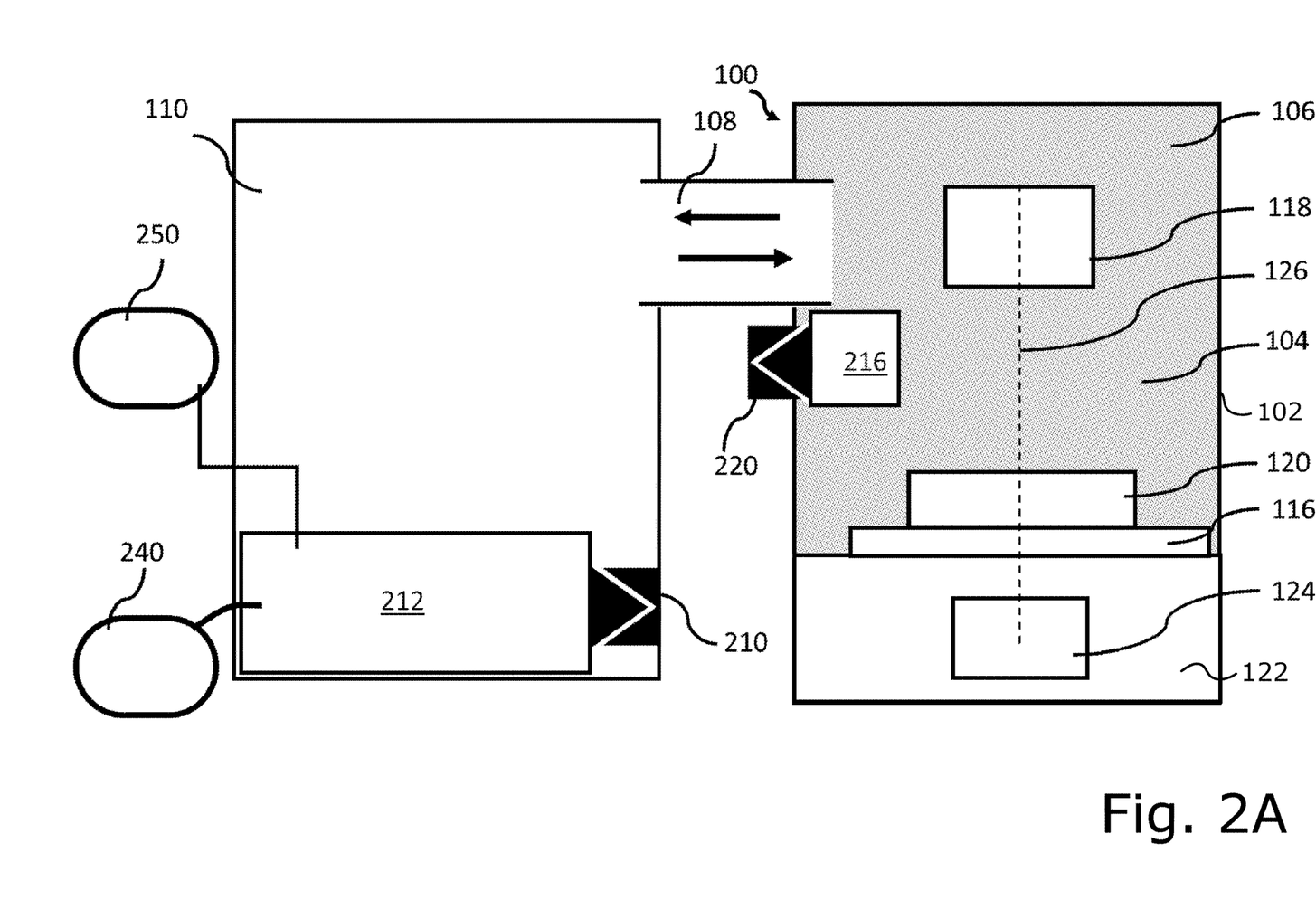
Figure 2B:
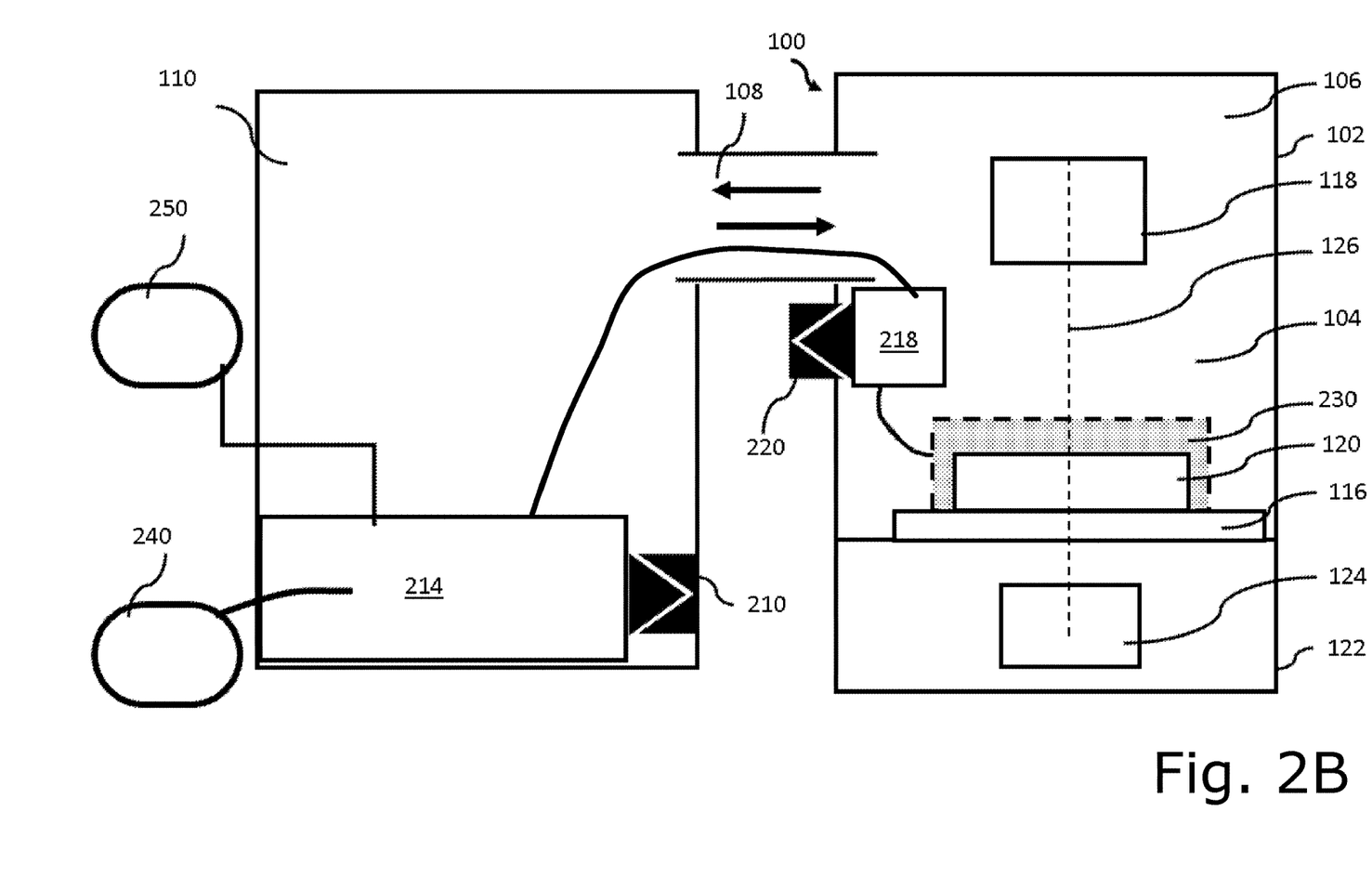
Figure 2C:
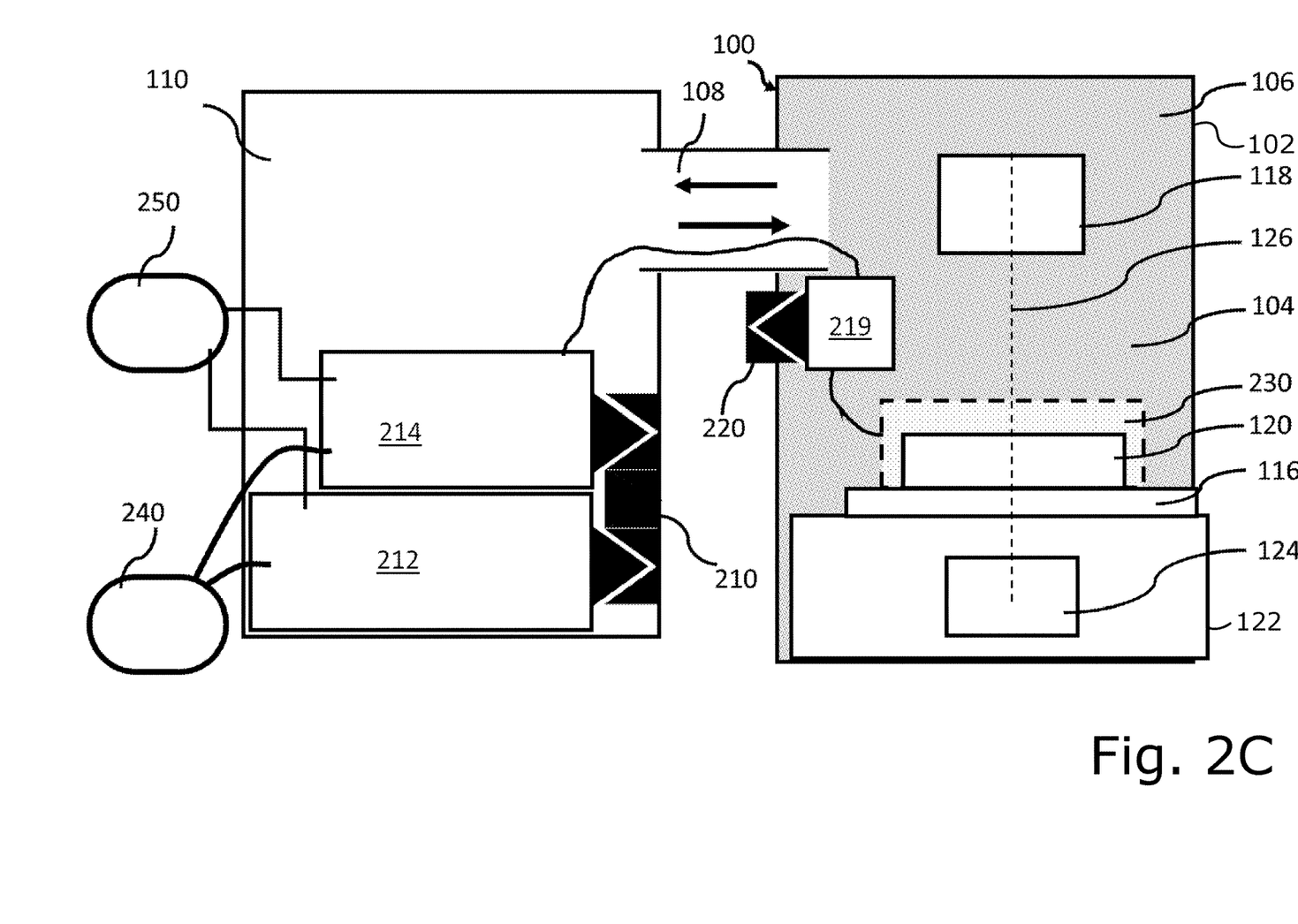

FIG. 2 shows schematically different configurations of embodiments of a system according to the inventive concept. The figures are described collectively, same reference signs depicting the same or at least functionally the same components.

FIG. 2A corresponds to the configuration as shown in FIG. 1. The microscope 100 is shown on the right side of FIG. 2A, the microscope 100 comprising as its main components the illumination optics 118, the microscope stage 116 and the imaging optics 124, the microscope objective defining an optical axis 126. The sample 120 is placed on the microscope stage 116 within the sample chamber 106 which is formed by the separated housing section 104 within the microscope housing 102 of the microscope 100. The imaging optics, or at least a part of it, is located in a second separated housing section 122. The incubation environment conditioning unit 110 is shown on the left side of FIG. 2A and is connected to the microscope 100 via the interface 108 in the housing section 104 of the microscope 100 and by conduits 114 extending from the conditioning unit 110 into the sample chamber 106.

The incubation environment conditioning unit 110 comprises a first pump control unit 212 which is connected to the pump control unit interface 210 and which is connected to a mutual/universal software interface 250 and to a common water pump 240. The mutual software interface 250 and the common water pump 240 can also be used in the second incubation mode as explained hereafter. The incubation environment conditioning unit 110 is designed for providing a first incubation atmosphere of a predefined flow rate, a predetermined temperature and with predefined contents of $H_2O$ and $CO_2$. The temperature control and the power supply of the conditioning unit 110 can also be used in the second incubation mode. The first incubation atmosphere is conducted via the interface 108 into the sample chamber 106. A part of the incubation atmosphere can also be discharged through the interface 108 and the conduits 114 as illustrated by the arrows. Within the sample chamber 106, there is arranged the first atmosphere regulation module 216 which is connected to the atmosphere regulation module interface 220. As already explained above, the first atmosphere regulation module 216 comprises sensors for detecting the temperature, and the contents of $CO_2$ and $H_2O$ in the incubation atmosphere. Depending on the actual values of these parameters, a feedback control can be implemented by communication of the first atmosphere regulation module 216 with the first pump control unit 212 for setting up the setpoint values of these parameters.

FIG. 2B shows an embodiment of a system 130 in the second incubation mode. In the following, only the differences to the embodiment shown in FIG. 2A will be explained. As shown in FIG. 2B, a stage top chamber 230 is placed or built within the sample chamber 106, the sample chamber 230 forming a relatively small volume around the sample 120 located within the stage top chamber 230. The first pump control unit 212 is replaced by a second pump control unit 214 which is connected to the same interface 210 shown in FIG. 2A. The second pump control unit 214 shares the same mutual software interface 250 and the same common water pump 240 as the first pump control unit 212. In the embodiment shown in FIG. 2B, a second atmosphere regulation module 218 replaces the first atmosphere regulation module 216 and is connected to the same interface 220 shown in FIG. 2A. In this configuration, the system 130 can be operated in the second incubation mode.

In the second incubation mode, the incubation environment conditioning unit 110, in this embodiment, generates a second incubation atmosphere of a predefined flow rate, a predetermined temperature and predetermined contents of $H_2O$, $CO_2$ and $O_2$. The second incubation atmosphere is conducted via interface 108 and via the second atmosphere regulation module 218 into the stage top chamber 230. As shown in FIG. 2B, corresponding supply lines are provided. The second atmosphere regulation module 218 comprises sensors for detecting the values of one or more parameters of the second incubation atmosphere, in this embodiment, sensors for detecting the temperature and the contents of $CO_2$, $H_2O$ and $O_2$. The temperature sensor can also be located within the stage top chamber 230 to more precisely detect the temperature within the stage top chamber 230. Again, the corresponding sensor signal allow a feedback control in order to supply the second incubation atmosphere with setpoint values of the corresponding parameters to the stage top chamber 230. Typically, hypoxia experiments are conducted in the second incubation mode where only a small volume of the stage top chamber 230 has to be flushed with $N_2$ as opposed to the large volume of the sample chamber 106 in the first incubation mode.

As can be seen from FIGS. 2A and 2B, one single system is provided for operation in two different incubation modes without the need to change systems or to convert/rebuild the system in order to switch from one incubation mode to the other.

FIG. 2C shows another embodiment of a system 130 according to the present inventive concept. Again, same reference signs depict same or at least functionally the same components. Only the differences to FIGS. 2A and 2B are explained in more detail. As can be seen from FIG. 2C, a common atmosphere regulation module 219 is connected to the atmosphere regulation module interface 220. This common atmosphere regulation module 219 is configured for controlling, in the first incubation mode, the first group of parameters of the first incubation atmosphere, and, in the second incubation mode, the second group of parameters of the second incubation atmosphere. It should be noted that this common atmosphere regulation module 219 can also be used in the embodiments according to FIGS. 2A and 2B such that no replacement of first and second atmosphere regulation modules would be necessary in order to switch from one incubation mode into the other.

The incubation environment conditioning unit 110 comprises a pump control unit interface 220 for connecting both the first and the second pump control units 212, 214 as shown in FIG. 2C. Each of the pump control units 212, 214 is connected to the mutual software interface 250 and to the common water pump 240. The configuration shown in FIG. 2C makes any replacements of pump control units and atmosphere regulation modules obsolete. The system may automatically detect the presence of a stage top chamber 230 within the sample chamber 106 and thus automatically switch into the second incubation mode. Alternatively, a user chooses the first or second incubation mode via a GUI. Concerning the remaining features and advantages of the configuration shown in FIG. 2C, reference is made to the previous explanations in connection with FIGS. 2A and 2B.

Figure 3:
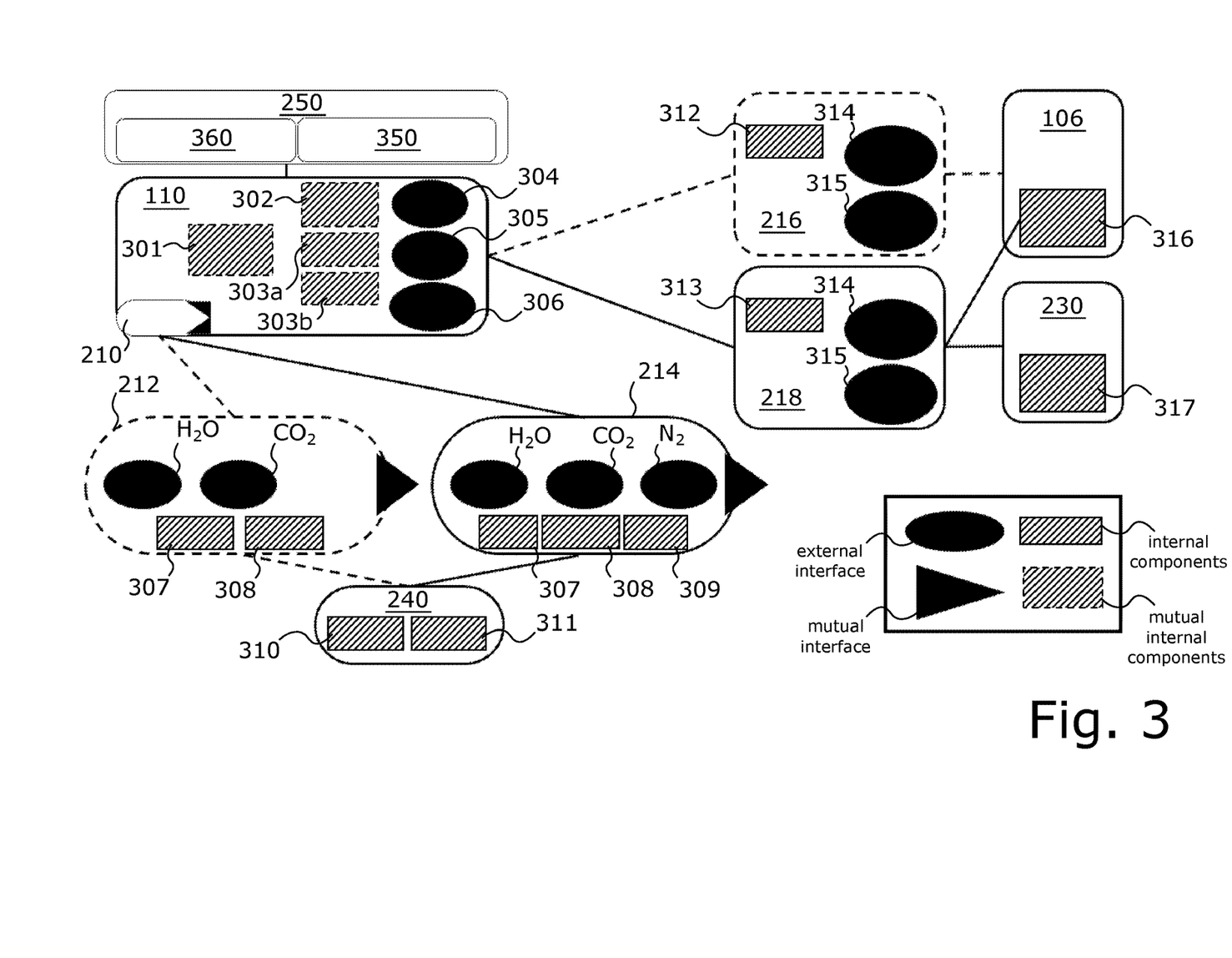

FIG. 3 schematically shows an embodiment of a system overview according to the inventive concept. In FIG. 3, a key is shown in the right corner below explaining the meaning of the symbols. The black elliptical symbol means an external interface, the black triangle means a mutual interface, the rectangle means an internal component, and the rectangle with the hatched frame means a mutual internal component. FIG. 3 shows an embodiment of a fully integrated system 130.

A universal software interface 250 is configured to control the system 130 in its entirety. To this end, the universal software interface 250 provides an incubation environment conditioning unit interface 360 and is, on the other hand, connected to the microscope controller 350. Thus, all functions and settings of the microscope 100 and of the incubation environment conditioning unit 110 can be controlled through the universal software interface 250 which typically provides a graphical user interface (GUI) which can be operated by a user.

The incubation environment conditioning unit 110 comprises an interface which is the pump control unit interface 210 shown in FIG. 2. First and/or second pump control units 212, 214 can be connected to this interface. The conditioning unit 110 further comprises a mechanical system interface 301, a main control PCB 302, a heating module 303*a* and a power supply 303*b* as mutual internal components. Such components are shared by the first and second incubation modes. Finally, the conditioning unit 110 comprises a power interface 304, a USB interface 305, and the water pump control interface 306 as mutual interfaces.

The first pump control unit 212 comprises an external interface for H2O-supply, an external interface for CO2-supply, as well as a control PCB 307 and a gas humidifier 308 as internal components. The second pump control unit 214 comprises an external interface for H2O-supply, an external interface for CO2-supply and an external interface for N2-supply and a communication connection to the incubation environment conditioning unit 110 (not shown). Further, as internal components, the second pump control unit 214 comprises a control PCB 307, a gas humidifier 308, and a gas mix module 309. A water pump 240 is connectable to the first and/or second pump control unit 212, 214, and comprises a water reservoir 310 and a water pump 311 as internal components.

In the embodiment shown in FIG. 3, the two incubation modes can be realized as already explained above in connection with FIGS. 1 and 2. As many components as possible are shared in the two incubation modes. The second pump control unit 214 is provided with means for humidifying the gas mixture in addition and independently from the incubation environment conditioning unit 110.

As already explained in connection with FIGS. 1 and 2, the incubation environment conditioning unit 110 communicates with the first and second atmosphere regulation modules 216 and 218. The first atmosphere regulation module 216 comprises a gas sensor 312 as an internal component, and an external interface 314 for an ambient temperature sensor. Optionally, an external interface 315 for a sample temperature sensor may be provided. While interface 314 connects to a temperature sensor in the sample chamber 106, interface 315 connects to a temperature sensor near the sample 120 itself. The second atmosphere regulation module 218 comprises a gas sensor 313 as an internal component and the same external interfaces 314 and 315 as module 216. As already mentioned above, it should be noted that in another embodiment the atmosphere regulation modules 216, 218 may comprise temperature sensors, on the one hand, and/or may be connected through corresponding external interfaces to gas sensors located in the sample chamber or in the stage top chamber. The gas sensors 312 and 313 include sensors for detecting the first and second group of parameters of the first and second incubation atmospheres, respectively. In case the external interface 315 of the second atmosphere regulation module 218 is missing, the temperature in the stage top chamber 230 is merely controlled via the temperature in the surrounding sample chamber 106.

The regulated/readjusted first incubation atmosphere is introduced into sample chamber 106 which comprises an ambient temperature sensor 316 which connects to interface 314 of module 216. On the other hand, a regulated/readjusted second incubation atmosphere is introduced into the stage top chamber 230 which may comprise a sample temperature sensor 317 which would connect to interface 315 of module 218. Alternatively, as explained above, the ambient temperature sensor 316 of sample chamber 106 connects to interface 314 of module 218.

In another embodiment, the second atmosphere regulation module 218 may comprise an external interface for water supply connected to a gas humidifier as an internal component. In this case, module 218 would be able to additionally and independently regulate/readjust the relative humidity in the second incubation atmosphere. In another alternative embodiment already discussed above, modules 216 and 218 are combined into a common atmosphere regulation module 219 (see FIG. 2C).

Figure 4:
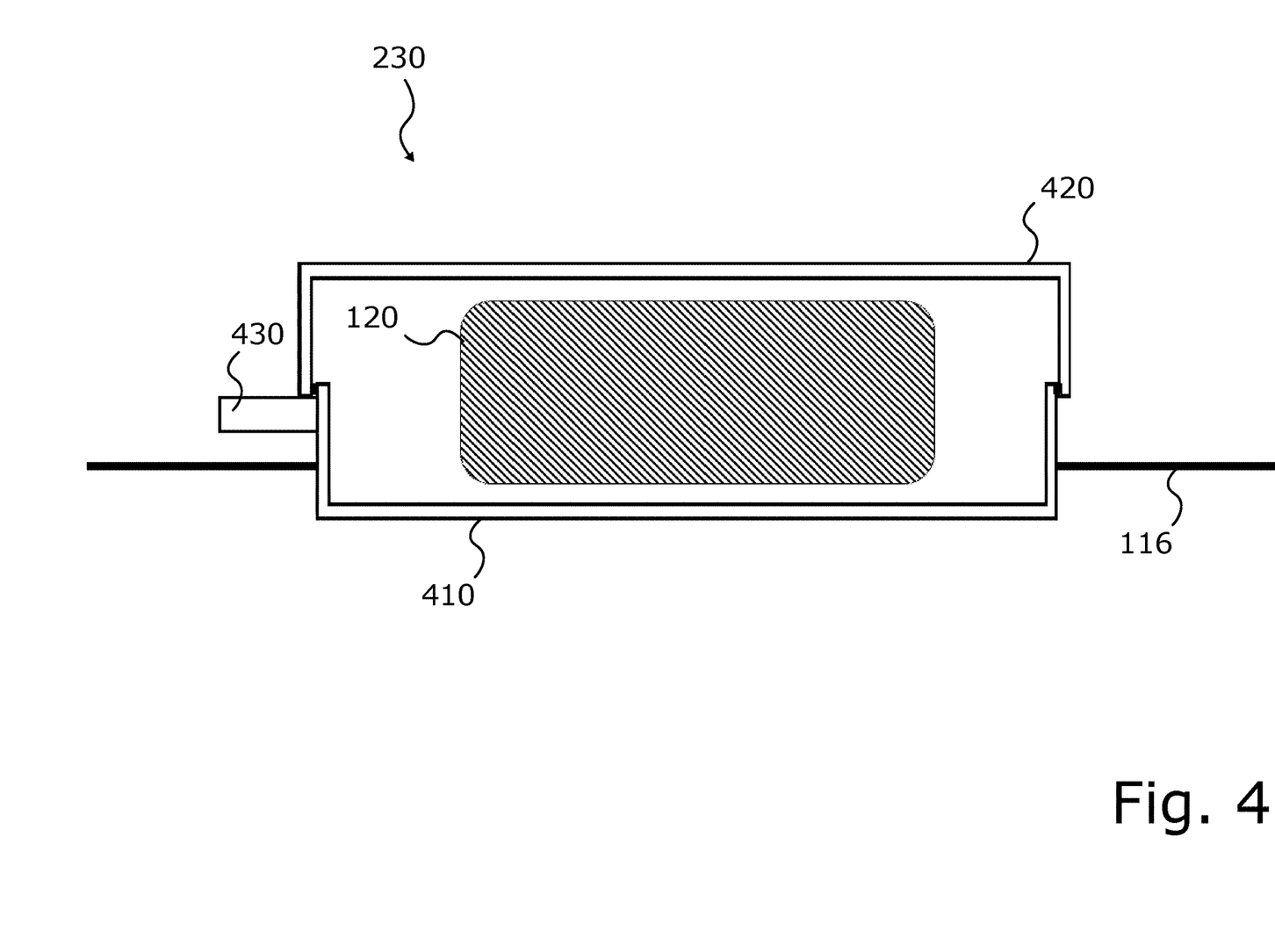

FIG. 4 schematically shows a cross section of an embodiment of a stage top chamber 230 preferably used in a system according to the present inventive concept. Hitherto, in the sample chamber incubation mode, a sample is placed on a sample holder on the microscope stage 116. In order to operate in the second incubation mode, a separate sample holder in the form of a stage top incubator had to be placed onto the microscope stage. The stage top chamber 230 shown in FIG. 4 overcomes this drawback by providing a universal sample holder 410 onto which a sample 120 is placed in both the first and second incubation modes. The universal sample holder 410 is located into or onto the microscope stage 116. A gas connection 430 is flanged at a side of the universal sample holder 410. By attaching a cover 420 to provide a sealed stage top chamber 230, in the second incubation mode, second incubation atmosphere is introduced into the stage top chamber 230 via a pipe connected to the gas connector 430.

LIST OF REFERENCE SIGNS 100 microscope
102 microscope housing
104 separated housing section
106 sample chamber
107 working surface
108 microscope interface
109 lid
110 incubation environment conditioning unit
112 opening
114 conduit
116 microscope stage
118 illumination optics
120 sample
122 second housing section
124 imaging optics
126 optical axis
130 system
140 controlling unit
142 display
210 pump control unit interface
212 first pump control unit
214 second pump control unit
216 first atmosphere regulation module
218 second atmosphere regulation module
219 common atmosphere regulation module
220 atmosphere regulation module interface
230 stage top chamber
240 water pump
250 universal software interface
301 mechanical system interface
302 main control PCB
303a heating module
303b power supply
304 power interface
305 USB interface
306 pump control interface
307 control PCB
308 gas humidifier
309 gas mix module
310 water reservoir
311 water pump
312 gas sensor
313 gas sensor
314 ambient temperature sensor interface
315 sample temperature sensor interface
316 ambient temperature sensor
317 sample temperature sensor
350 microscope controller
360 incubation environment conditioning unit interface
410 universal sample holder
420 cover
430 gas connector

What is claimed is:

1. A system for microscopic examination of a sample comprising:
  a microscope and an incubation environment conditioning unit connected to said microscope, the microscope comprising:
    a microscope housing enclosing an illumination optics, a microscope stage and an imaging optics;
    an integrated sample chamber located within the microscope housing and formed by a separated housing section within said microscope housing, the integrated sample chamber being configured to connect to a first pump control unit and to a first atmosphere regulation module;
  the housing section comprising a microscope interface configured for connecting the incubation environment conditioning unit to the integrated sample chamber and to a stage top chamber when the stage top chamber is placed within the sample chamber and configured to receive the sample, the stage top chamber being configured to connect to a second pump control unit and to a second atmosphere regulation module;
  the first pump control unit being configured to connect to a pump control unit interface, and the second pump control unit being configured to connect to the pump control unit interface;
  a universal software interface for communication with a microscope controller, the microscope controller being configured to control the illumination optics, the microscope stage and the imaging optics of the microscope for controlling the microscopic examination of the sample, and for providing an incubation environment conditioning unit interface for communication with the incubation environment conditioning unit such that the microscope and the incubation environment conditioning unit can both be controlled by the universal software interface;
  wherein the incubation environment conditioning unit is configured to provide a first incubation mode by using the first pump control unit to supply a first incubation atmosphere to the integrated sample chamber, and/or a second incubation mode by using the second pump control unit to supply a second incubation atmosphere to the stage top chamber; and
  wherein the universal software interface is configured such that the system automatically switches into the first incubation mode if the first pump control unit is connected to the pump control unit interface, and into the second incubation mode if the second pump control unit is connected to the pump control unit interface.

2. The system of claim 1, wherein the first pump control unit is configured to supply the first incubation atmosphere characterized by a first group of parameters in the first incubation mode, and wherein the second pump control unit is configured to supply the second incubation atmosphere characterized by a second group of parameters in the second incubation mode.

3. The system of claim 2, wherein the microscope comprises a common atmosphere regulation module for controlling the first group of parameters of the first incubation atmosphere in the first incubation mode, and the second group of parameters of the second incubation atmosphere in the second incubation mode.

4. The system of claim 3, wherein the common atmosphere regulation module is configured to communicate with the first pump control unit in the first incubation mode, and with the second pump control unit in the second incubation mode.

5. The system of claim 2, wherein the microscope comprises an atmosphere regulation module interface for connecting the first atmosphere regulation module and/or the second atmosphere regulation module, wherein the first atmosphere regulation module is configured for controlling the first group of parameters of the first incubation atmosphere in the first incubation mode, and wherein the second atmosphere regulation module is configured for controlling the second group of parameters of the second incubation atmosphere in the second incubation mode.

6. The system of claim 5, wherein the atmosphere regulation module interface is configured for connecting the first atmosphere regulation module and for alternatively connecting the second atmosphere regulation module when the first atmosphere regulation module is not connected to the atmosphere regulation module interface.

7. The system of claim 5, wherein the first atmosphere regulation module comprises sensors for determining the temperature and/or the contents of $H_2O$ and/or $CO_2$ in the incubated sample chamber.

8. The system of claim 5, wherein the second atmosphere regulation module comprises sensors for determining the temperature and/or the contents of $O_2$ and/or $H_2O$ and/or $CO_2$ in the incubated stage top chamber.

9. The system of claim 5, wherein the second atmosphere regulation module further comprises a humidifier for humidifying the second incubation atmosphere.

10. The system of claim 9, further comprising a common water pump configured to supply water to both the first and the second pump control units.

11. The system of claim 2, wherein the first group of parameters and second group of parameters each comprises at least one of a flow rate and a temperature and contents of water and/or $CO_2$ and/or $N_2$ and/or $O_2$.

12. The system of claim 1, wherein the pump control unit interface is configured for connecting the first pump control unit, and for alternatively connecting the second pump control unit when the first pump control unit is not connected to the pump control unit interface.

13. The system of claim 1, wherein the pump control unit interface is configured for connecting both the first pump control unit and the second pump control unit.

14. The system of claim 1, wherein the system is configured to use the same temperature control in the first incubation mode and in the second incubation mode to control the temperature in the stage top chamber via the temperature in the integrated sample chamber.

15. The system of claim 1 further comprising a sample holder for holding the sample in the first incubation mode, the sample holder being adapted for attachment of a cover for forming the stage top chamber to be used in the second incubation mode.

16. The system of claim 1, wherein the housing section comprises a lid providing direct access to the microscope stage for placing the sample and/or the stage top chamber in the sample chamber.

17. The system of claim 1, wherein the integrated sample chamber does not comprise the imaging optics.

* * * * *